United States Patent [19]

Horodysky et al.

[11] Patent Number: 4,465,605
[45] Date of Patent: Aug. 14, 1984

[54] BORATED POLYHYDROXYALKYL SULFIDES AND LUBRICANTS CONTAINING SAME

[75] Inventors: Andrew G. Horodysky, Cherry Hill; Joan M. Kaminski, Mullica Hill, both of N.J.

[73] Assignee: Mobil Oil Corporation, New York, N.Y.

[21] Appl. No.: 434,803

[22] Filed: Oct. 18, 1982

[51] Int. Cl.$^3$ ............................................... C10M 1/54
[52] U.S. Cl. .................................. 252/46.3; 252/49.6; 260/462 R
[58] Field of Search ............................ 252/46.3, 49.6; 260/462 R

[56] References Cited

U.S. PATENT DOCUMENTS

| | | | |
|---|---|---|---|
| 2,526,506 | 10/1950 | Rogers et al. | 260/462 R |
| 3,303,130 | 2/1967 | Scypinski et al. | 260/462 R |
| 4,115,286 | 9/1978 | Baldwin et al. | 252/46.3 |
| 4,394,277 | 7/1983 | Small, Jr. | 252/48.2 |

Primary Examiner—Andrew Metz
Attorney, Agent, or Firm—Alexander J. McKillop; Michael G. Gilman; Claude E. Setliff

[57] ABSTRACT

Lubricant and liquid fuel compositions contain a friction reducing or antioxidant additive. The additive is a borated trihydroxy hydrocarbyl sulfide.

17 Claims, No Drawings

BORATED POLYHYDROXYALKYL SULFIDES AND LUBRICANTS CONTAINING SAME

BACKGROUND OF THE INVENTION

1. Field of the Invention

The invention relates to lubricant and liquid fuel compositions. In particular, it relates to the use of borated trihydroxy hydrocarbyl sulfides in liquid fuels and lubricants to reduce friction and fuel consumption in internal combustion engines.

2. Discussion of the Related Art

It is known that sliding or rubbing metal or other solid surfaces are subject to wear under conditions of extreme pressure. Wearing is particularly acute in modern engines in which high temperatures and contact pressures are prevalent. Under such conditions, severe erosion of metal surfaces can take place even with present generation lubricants unless a load carrying or antiwear additive is present herein.

Friction is also a problem any time two surfaces are in sliding or rubbing contact. It is of special significance in an internal combustion engine and related power train components, because loss of a substantial amount of the theoretical mileage possible from a gallon of fuel is traceable directly to friction.

With respect to the novel compounds of this invention, no art is known that teaches or suggests them, or their use in lubricants or fuels. There are, however, patents that disclose certain sulfur-containing materials. They include, for example, U.S. Pat. No. 3,361,723 which discloses a thiol-containing polyether and a process for its preparation and U.S. Pat. No. 4,244,827 teaches mixtures of di- or trithiophosphate acid diesters produced from 1,2-diols or 1-mercapto-2-hydroxy compounds and $P_2S_5$.

SUMMARY OF THE INVENTION

In accordance with the invention there is provided a lubricant or liquid fuel composition comprising a major amount of a lubricant or fuel and a friction reducing or antioxidant amount of a product made by reacting a sulfide of the formula $$(HO)_x RSR'(OH)_y$$

wherein R and R' are $C_1$ to $C_{30}$ hydrocarbyl groups or mixtures thereof, the total of carbon atoms from R and R' being from 13 to 33, and either of x and y is 0 to 3, the sum thereof being at least 3, with a boron compound such as boric acid, boric oxide, or an alkyl borate of the formula $(RO)_a B(OH)_b$ wherein R is a $C_3$ to $C_6$ alkyl group, a is 1 to 3 and b is 0 to 2, the sum being 3. It will be understood that all the OH groups can be attached to R or R' or to R and R' and that they can be attached to any carbons in the group. It is not necessary, for example, that they be on adjacent carbon atoms.

DESCRIPTION OF SPECIFIC EMBODIMENTS

The sulfides can be made by any process known to the art. For example, they can be made by reacting a mercaptoglycerol, a phase transfer agent, such as , used to enhance the solubility of the mercapticle in situ, sodium hydroxide or other alkali metal hydroxide and a hydrocarbyl epoxide, e.g., a $C_{15}$–$C_{18}$ alkyl epoxide. In this reaction, the mercaptide is formed first, followed by the addition of the epoxide. The product obtained is

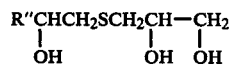

wherein R'' is a $C_{13}$–$C_{16}$ hydrocarbyl group.

In preparing the sulfides, we prefer to use equimolar amounts of mercaptoglycerol and epoxide. The sodium hydroxide or other alkali metal hydroxide can be used in excess of theoretical, the maximum being about 10%, but we prefer no more than 2 to 5% excess. Further, we have found that the optimum amount of phase transfer catalysts (PTC) is somewhere within the range of about 0.02 to 0.1 mole of PTC per mole of epoxide. The reaction can be carried out at from about 35° C. to about 100° C., preferably about 60° C. to 95° C., in from 0.5 to 5 hours, preferably 1 to 3 hours. Solvents for this reaction include the hydrocarbon solvents, such as benzene, toluene, xylene and the like. Water should be used as a solvent in this reaction.

The sulfide formed is reacted with an equimolar amount of the boron compound, preferably at a temperature of from about 75° C. to about 150° C. To assure complete boration, we prefer to use an excess of from about 5% to about 30% of boron compound over the theoretical amount required. In carrying out the reaction, alcohol solvents, such as propanol and butanol, are preferred, but they can be used in combination with hydrocarbon solvents such as benzene and toluene.

As indicated hereinabove, the additives are reaction products. We do not know what the precise makeup of the product is, but we believe it contains amounts of one or more of the following compounds:

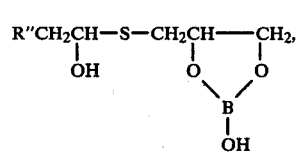

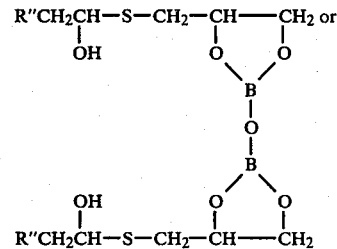

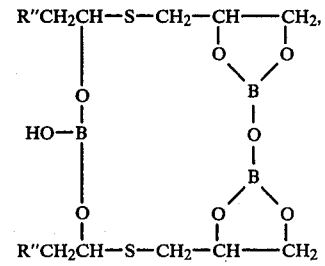

-continued

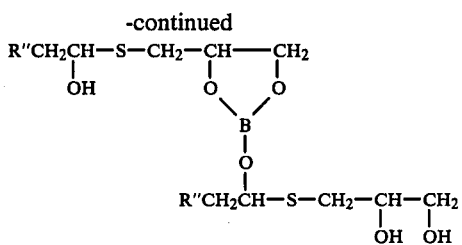

It will be understood that the mixed alkyl epoxide can be obtained by mixing the respective epoxides in their desired proportions, or the reaction mixtures used to prepare them can be ordered so they are obtained directly as the reaction product.

The borated sulfides are used with lubricating oils and greases to the extent of from about 0.1% to about 10% by weight of the total composition. Furthermore, other additives, such as detergents, dispersants, viscosity index improvers, pour depressants, anti-oxidants, inhibitors, anti-wear agents and the like may be present. These can include phenates, sulfonates, succinimides, zinc dithiophosphates, polymers, calcium and magnesium salts and the like.

The lubricants contemplated for use with the esters herein disclosed include mineral and synthetic hydrocarbon oils of lubricating viscosity, mixtures of mineral oils and synthetic oils and greases from any of these, including mixtures. The synthetic hydrocarbon oils include long-chain alkanes such as cetanes and olefin polymers such as oligomers of hexane, octane, decene, and dodecene, etc. The compounds of the invention are especially effective in synthetic oils formulated using mixtures of synthetic hydrocarbon olefin oligomers and lesser amounts of hydrocarbyl carboxylate ester fluids. The other synthetic oils, which can be used alone with the borated compounds of this invention, or which can be mixed with a mineral or synthetic hydrocarbon oil, include (1) fully esterified ester oils, with no free hydroxyls, such as pentaerythritol esters of monocarboxylic acids having 2 to 20 carbon atoms trimethylolpropane esters of monocarboxylic acids having 2 to 20 carbon atoms, (2) polyacetals and (3) siloxane fluids. Especially useful among the synthetic esters are those made from polycarboxylic acids and monohydric alcohols. More preferred are the ester fluids made by fully esterifying pentaerythritol, or mixtures thereof with di- and tripentaerythritol, with an aliphatic monocarboxylic acid containing from 1 to 20 carbon atoms, or mixtures of such acids.

A wide variety of thickening agents can be used in the greases of this invention. Included among the thickening agents are alkali and alkaline earth metal soaps of fatty acids and fatty materials having from about 12 to about 30 carbon atoms per molecule. The metals are typified by sodium, lithium, calcium and barium. Fatty materials are illustrated by stearic acid, hydroxystearic acid, stearin, cottonseed oil acids, oleic acid, palmitic acid, myristic acid and hydrogenated fish oils.

Other thickening agents include salt and salt-soap complexes as calcium stearate-acetate (U.S. Pat. No. 2,197,263), barium stearate-acetate (U.S. Pat. No. 2,564,561), calcium stearate-caprylate-acetate complexes (U.S. Pat. No. 2,999,065), calcium caprylate-acetate (U.S. Pat. No. 2,999,066), and calcium salts and soaps of low-, intermediate- and high-molecular weight acids and of nut oil acids.

Another group of thickening agents comprises substituted ureas, phthalocyanines, indanthrene, pigments such as perylimides, pyromellitdiimides, and ammeline.

The preferred thickening gelling agents employed in the grease compositions are essentially hydrophobic clays. Such thickening agents can be prepared from clays which are initially hydrophilic in character, but which have been converted into a hydrophobic condition by the introduction of long chain hydrocarbon radicals into the surface of the clay particles; prior to their use as a component of a grease composition, as, for example, by being subjected to a preliminary treatment with an organic cationic surface active agent, such as an onium compound. Typical onium compounds are tetraalkylammonium chlorides, such as dimethyl dioctadecyl ammonium chloride, dimethyl dibenzyl ammonium chloride and mixtures thereof. This method of conversion, being well known to those skilled in the art, is believed to require no further discussion, and does not form a part of the present invention. More specifically, the clays which are useful as starting materials in forming the thickening agents to be employed in the grease compositions, can comprise the naturally occurring chemically unmodified clays. These clays are crystalline complex silicates, the exact composition of which is not subject to precise description, since they vary widely from one natural source to another. These clays can be described as complex inorganic silicates such as aluminum silicates, magnesium silicates, barium silicates, and the like, containing, in addition to the silicate lattice, varying amounts of cation-exchangeable groups such as sodium. Hydrophilic clays which are particularly useful for conversion to desired thickening agents include montmorillonite clays, such as bentonite, attapulgite, hectorite, illite, saponite, sepiolite, biotite, vermiculite, zeolite clays, and the like. The thickening agent is employed in an amount from about 0.5 to about 30, and preferably from 3 percent to 15, percent by weight of the total grease composition.

The liquid fuels contemplated include liquid hydrocarbon fuels such as fuel oils, diesel oils and gasolines and alcohol fuels such as methanol and ethanol or mixtures of these fuels. Concentrations of additive in the fuel may be from about 10 lb. to about 1000 lb. per 1000 bbl of fuel, preferably from about 26 lb. to about 250 lb. per 1000 bbl.

Having described the invention in general terms, the following are offered to specifically illustrate the development. It is to be understood they are illustrations only and that the invention shall not be limited except as limited by the appended claims.

EXAMPLE 1

Synthesis of 1-($\beta$-hydroxy)pentadecyl-octadecyl sulfide-2,3-dihydroxy Propane A mixture of 90% 1-mercaptoglycerol (56.7 g), methyltri($C_8$–$C_{10}$) alkyl ammonium chloride (10.9 g), 50% sodium hydroxide (38 g), toluene (40 cc) and water (20 cc) were stirred at room temperature. The reaction temperature rose to 69° C. 1,2-$C_{15}$–$C_{18}$ alkyl epoxide (114.7 g [about 28% $C_{15}$, about 28% $C_{16}$, about 28% $C_{17}$, and about 16% $C_{18}$]) were added dropwise over a period of 2½ hours. The vigorously agitated reaction mixture thickened appreciable upon addition of epoxide, and an additional 300 cc of toluene and 100 cc of water are added. The reaction was refluxed for one hour and transferred hot to a 2-liter separatory funnel.

After sitting overnight the water layer separated easily from the toluene layer with heating. The acidified wash contained no 1-mercaptoglycerol. The toluene solution was washed with water (2×100 cc) and dried over MgSO$_4$·Na$_2$SO$_4$. The solution was filtered, and the solvent was removed by high speed rotary evaporation to yield a tan waxy solid.

EXAMPLE 2

Synthesis of 1-($\beta$-hydroxy)pentadecyl-octadecyl Sulfide-2,3-dihydroxy Propane Borate A solution of 1-($\beta$-hydroxy)C$_{15}$–C$_{18}$ alkyl sulfide-2,3-dihydroxy propane (50 g), prepared as described in Example 1, n-butanol (20 g), and toluene (60 g) was heated to 60° C., and boric acid (8.8 g) was added to a reaction vessel. The expected amount of water was removed by azeotropic distillation with a maximum reaction temperature of 115° C. The reaction solution was filtered through diatomaceous earth. Solvent was removed by high speed rotary evaporation to yield a pale yellow, waxy solid product.

EXAMPLE 3

Synthesis of 1-($\beta$-hydroxy)tetradecyl Sulfide-2,3-dihydroxy Propane

A mixture of 90% 1-mercaptoglycerol (113.4 g), methyl tri(C$_8$–C$_{10}$) alkyl ammonium chloride (21.8 g), 50% sodium hydroxide (76 g), toluene (80 cc), and water (40 cc) was stirred at room temperature. The reaction temperature rose to 75° C. 1,2-tetradecyl epoxide (200 g) was added dropwise over a period of 1 hour, and the reaction temperature remained between 75° and 78° C. during addition. The reaction mixture became very viscous after the addition, and an additional 60 cc of toluene and 60 cc of water were added. The reaction mixture was refluxed at 92° C. for 1 hour and transferred hot to a separatory funnel. Approximately 400 cc of toluene and 200 cc of water were added. After the water wash, the toluene solution was filtered through diatomaceous earth. Solvent was removed by high speed rotary evaporation to yield a tan waxy solid.

EXAMPLE 4

Synthesis of 1-($\beta$-hydroxy)tetradecyl Sulfide-2,3-dihydroxy Propane Borate

A solution of 1-($\beta$-hydroxy)tetradecyl sulfide-2,3-dihydroxy propane prepared as described in Example 3, n-butanol (20 g), and toluene (60 g) was heated to 55° C., and boric acid (11.2 g) was added. Water was removed by azeotropic distillation with a maximum reaction temperature of 110° C. The reaction solution was filtered through diatomaceous earth. Solvent was removed by high speed rotary evaporation to yield a pale yellow, waxy solid product.

EVALUATION OF PRODUCTS

The compounds were evaluated as friction modifiers in accordance with the following test.

Low Velocity Friction Apparatus

Description

The Low Velocity Friction Apparatus (LVFA) is used to measure the friction of test lubricants under various loads, temperatures, and sliding speeds. The LVFA consists of a flat SAE 1020 steel surface (diameter 1.5 in.) which is attached to a drive shaft and rotated over a stationary, raised, narrow ringed SAE 1020 steel surface (area 0.08 in.$^2$). Both surfaces are submerged in the test lubricant. Friction between the steel surfaces is measured as a function of the sliding speed at a lubricant temperature of 250° F. The friction between the rubbing surfaces is measured using a torque arm-strain gauge system. The strain gauge output, which is calibrated to be equal to the coefficient of friction, is fed to the Y axis of an X-Y plotter. The speed signal from the tachometer-generator is fed to the X-axis. To minimize external friction, the piston is supported by an air bearing. The normal force loading the rubbing surfaces is related by air pressure on the bottom of the piston. The drive system consists of an infinitely variable-speed hydraulic transmission driven by a ½ HP electric motor. To vary the sliding speed, the output speed of the transmission is regulated by a lever-cam motor arrangement.

Procedure

The rubbing surfaces and 12–13 ml of test lubricant are placed on the LVFA. A 240 psi load is applied, and the sliding speed is maintained at 40 fpm at ambient temperature for a few minutes. A plot of coefficients of friction (U$_k$) over the range of sliding speeds, 5 to 40 fpm (25–195 rpm), is obtained. A minimum of three measurements is obtained for each test lubricant. Then, the test lubricant and specimens are heated to 250° F., another set of measurements is obtained, and the system is run for 50 minutes at 250° F., 240 psi and 40 fpm sliding speed. Afterward, measurements of U$_k$ vs. speed are taken at 240, 300, 400, and 500 psi. Freshly polished steel specimens are used for each run. The surface of the steel is parallel ground to 4–8 microinches.

The data obtained are shown in Table 1. The data in Table 1 are reported as percent reduction in coefficient of friction at two speeds. The fully formulated 5 W-30 synthetic lubricating oil had the following general characteristics:

| | |
|---|---|
| Viscosity 100° C. | 10.6 cs |
| Viscosity 40° C. | 57.7 cs |
| Viscosity Index | 172 |

TABLE 1

| | Friction Characteristics Using Low Velocity Friction Apparatus | | |
|---|---|---|---|
| | Additive Conc. | Reduction or % Change in Coefficient of Friction | |
| Additive | Wt. % | 5 Ft./Min. | 30 Ft./Min. |
| Base Oil | 0 | 0 | 0 |
| Example 2 | 1 | 39 | 27 |
| Example 4 | 1 | 51 | 39 |

We claim:

1. A product made by reacting a sulfide of the formula (HO)$_x$RSR'(OH)$_y$ wherein R and R' are C$_1$ to C$_{30}$ hydrocarbyl groups or mixtures thereof, the total of carbon atoms from R and R' being from 13 to 33, and either of x and y is 0 to 3, the sum thereof being at least 3, with at last an equimolar amount of a boron compound, the reaction being carried out at from about 75° C. to about 150° C.

2. The product of claim 1 wherein the boron compound is boric oxide or is of the formula:

$(RO)_aB(OH)_b$ wherein a is 1 to 3 and b is 0 to 2, the sum of a and b being 3.

3. The product of claim 1 wherein the sulfide is hydroxy pentadecyl-octadecyl sulfide-2,3-dihydroxy propane.

4. The product of claim 3 wherein the boron compound is boric acid.

5. The product of claim 1 wherein the sulfide is hydroxy tetradecyl sulfide-2,3-dihydroxy propane.

6. The product of claim 5 wherein the boron compound is boric acid.

7. A lubricant composition comprising a major amount of a lubricant selected from the group consisting of oils of lubricating viscosity and greases thereof and a friction reducing amount of a product made by reacting a sulfide of the formula $(HO)_xRSR'(OH)_y$ wherein R and R' are $C_1$ to $C_{30}$ hydrocarbyl groups, or mixtures thereof, the total of carbon atoms from R and R' being from 13 to 33, and either of x and y is 0 to 3, the sum thereof being at least 3, with at least an equimolar amount of a boron compound, the reaction being carried out at from about 75° C. to about 150° C.

8. The composition of claim 7 wherein the boron compound is boric oxide or is of the formula:

$(RO)_aB(OH)_b$ wherein a is 1 to 3 and b is 0 to 2, the sum of a and b being 3.

9. The composition of claim 7 wherein the sulfide is hydroxy pentadecyl-octadecyl sulfide-2,3-dihydroxy propane.

10. The composition of claim 9 wherein the boron compound is boric acid.

11. The composition of claim 7 wherein the sulfide is hydroxy tetradecyl sulfide-2,3-dihydroxy propane.

12. The composition of claim 11 wherein the boron compound is boric acid.

13. The composition of claim 7 wherein the lubricant is (1) a mineral oil, (2) a synthetic oil, (3) a mixture of these, or (4) a grease from (1), (2) or (3).

14. The composition of claims 7, 8, 9, 10, 11, 12 or 13 wherein the lubricant is a synthetic lubricating oil.

15. The composition of claim 7 wherein the lubricant is a mineral oil.

16. The composition of claim 7 wherein the lubricant is a grease.

17. The composition of claim 13 wherein the lubricant is a mixture of mineral and synthetic oils.

* * * * *

UNITED STATES PATENT AND TRADEMARK OFFICE
CERTIFICATE OF CORRECTION

PATENT NO. : 4,465,605
DATED : August 14, 1984
INVENTOR(S) : Andrew G. Horodysky and Joan M. Kaminski It is certified that error appears in the above-identified patent and that said Letters Patent is hereby corrected as shown below:

Col. 3, line 32, "octane" should be --octene--.

Col. 4, line 67, "are" should be --were--.

Col. 6, line 11, "related" should be --regulated--.

Col. 6, line 63, "last" should be --least--.

Signed and Sealed this

Fifth Day of March 1985

[SEAL]

Attest:

DONALD J. QUIGG

Attesting Officer

Acting Commissioner of Patents and Trademarks